(12) United States Patent
Nagasaka et al.

(10) Patent No.: US 7,609,864 B2
(45) Date of Patent: Oct. 27, 2009

(54) FINGER IDENTIFICATION METHOD AND APPARATUS

(75) Inventors: Akio Nagasaka, Kokubunji (JP); Naoto Miura, Kokubunji (JP); Takafumi Miyatake, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 987 days.

(21) Appl. No.: 11/263,869

(22) Filed: Nov. 2, 2005

(65) Prior Publication Data

US 2006/0098848 A1 May 11, 2006

(30) Foreign Application Priority Data

Nov. 5, 2004 (JP) ............................. 2004-321454
Aug. 26, 2005 (JP) ............................. 2005-245241

(51) Int. Cl.
*G06K 9/00* (2006.01)

(52) U.S. Cl. ..................................... 382/124
(58) Field of Classification Search ................. 382/115, 382/124, 128–129, 190, 209, 218; 340/5.52, 340/5.53, 5.8, 5.82, 5.83; 356/71; 396/15; 713/186; 902/3
See application file for complete search history.

(56) References Cited

U.S. PATENT DOCUMENTS

| 6,173,068 | B1 * | 1/2001 | Prokoski ..................... 382/115 |
| 6,970,234 | B2 * | 11/2005 | Nagasaka et al. ............. 356/71 |
| 7,123,755 | B2 * | 10/2006 | Shigeta ....................... 382/124 |
| 7,245,745 | B2 | 7/2007 | Nagasaka et al. |
| 2002/0048014 | A1 | 4/2002 | Kono et al. |
| 2004/0184641 | A1 | 9/2004 | Nagasaka et al. |

FOREIGN PATENT DOCUMENTS

DE 103 32 106 A1 9/2004
WO WO 00/39744 7/2000

OTHER PUBLICATIONS

Chinese Office Action in corresponding Chinese patent application No. 2005101186901, Sep. 19, 2008.

* cited by examiner

*Primary Examiner*—Daniel G Mariam
(74) *Attorney, Agent, or Firm*—Brundidge & Stanger, P.C.

(57) ABSTRACT

An image pickup scheme capable of always providing an optimum quality of a blood vessel pattern, in image pickup of a blood vessel pattern of a finger using transmitted light, without being affected by a difference, if any, in an external environment. A personal identification apparatus includes light sources for irradiating light to be transmitted by a finger, an image pickup unit for picking up an image using light transmitted by the finger, finger detection unit for detecting that the finger exists in a predetermined position, finger region extraction unit for extracting a region occupied by the finger from an image picked up by the image pickup unit, and gain changing unit for changing an amplification factor of image pickup elements in the image pickup unit on the basis of a picture quality of a specific region within the extracted region.

15 Claims, 10 Drawing Sheets

FINGER IDENTIFICATION METHOD AND APPARATUS

CROSS-REFERENCE TO RELATED APPLICATION

The present invention is related to U.S. application Ser. No. 10/617,828 filed Jul. 14, 2003, the entire content of which is incorporated herein by reference.

INCORPORATION BY REFERENCE

The present application claims priorities from Japanese applications JP 2005-245241 filed on Aug. 26, 2005, JP 2004-321454 filed on Nov. 5, 2004, the contents of which are hereby incorporated by reference into this application.

BACKGROUND OF THE INVENTION

The present invention relates to a personal identification apparatus using a living body. In particular, the present invention relates to a biometric personal identification apparatus based on a blood vessel (vein) pattern of a finger.

As a security scheme that does not need carrying a key or the like, that is high in convenience, and that is little fear of illegal use such as loss and theft, attention is paid to biometrics using a part of an individual's body, such as a finger print, iris, a blood vessel (vein) pattern. Among them, the identification method using a blood vessel pattern does not remind of criminal investigation unlike the identification method using a fingerprint. The identification method using a blood vessel pattern does not irradiate light directly to an eyeball unlike the identification method using iris. Therefore, the identification method using a blood vessel pattern causes little psychological resistance feeling. Furthermore, since the blood vessel pattern is not a feature of a living body surface which can be observed easily, but it is an inside feature, the identification method using a blood vessel pattern has an advantage that the residual property is not present and forgery is difficult.

Such a blood vessel pattern within a living body is obtained by illuminating a target region with near-infrared light sources and picking up an image of the target region with an image pickup system, such as a camera or an image sensor, having a sensitivity for near-infrared light (see, for example, US2004/0184641). Since hemoglobin in blood absorbs near-infrared light well, light is absorbed by a blood vessel and the blood vessel is taken dark as compared with a peripheral tissue. A pattern generated by the difference between brightness and darkness becomes the blood vessel pattern.

In such a scheme for picking up an image of a blood vessel pattern using light, existence of light other than light from the infra-red light sources for image pickup, i.e., external light remarkably affects the quality of the blood vessel pattern image picked up. In most biometric schemes using light used heretofore, therefore, restrictions have been imposed on the use condition under the external light. For example, when the biometric scheme is used outdoors in clear weather, light having near-infrared wavelengths is also included in naturally existing sunlight and its intensity is far higher than that of the output of the light sources for blood vessel pattern image pickup. If sunlight streams into an identification apparatus including a camera adjusted so as to be able to optimally pick up an image of a slight difference between bright light and dark light as a pattern, luminance of many pixels is saturated at its maximum value because of intense light, and an image including a saturated highlight region is obtained. In such a saturated highlight region, the luminance is uniquely at the maximum value. Therefore, the difference between brightness and darkness in the blood vessel portion does not appear, and a correct blood vessel pattern cannot be obtained.

In the invention described in US2004/0184641, a method of adjusting the brightness of the light sources for image pickup according to various finger states has been disclosed as the method for picking up an image of a blood vessel pattern clearly. However, the method is premised on the indoor use, and the supposed range of the external light variation is also limited. Under the intense external light as described above, the saturated highlight region cannot be eliminated in many cases even if the intensity of the light sources is minimized. Furthermore, in the case described above, light irradiated to the finger cannot be utilized suitably although it has a quantity enough to pick up an image of the blood vessel pattern. As a result, energy is supplied to the light sources dedicated to image pickup unnecessarily.

A conceivable solution to the problem is to eliminate the saturated highlight region by using sensitivity adjustment, such as the exposure or iris of the image pickup camera, together. In ordinary photographing as well, the sensitivity, such as the exposure or iris, of the camera is adjusted and the brightness of illumination such as the light is suitably changed. Basically, this should be conducted automatically. Not a few cameras have a mechanism called AGC (auto gain control) as a standard component. The AGC is a function of amplifying an output of image pickup elements, such as CCDs (Charge-Coupled Devices), in a camera to bring the output into a predetermined voltage range. Specifically, the amplification factor of the amplifier is automatically adjusted. The amplification factor is increased when the output of the image pickup elements as a whole is low. Conversely, the amplification factor is decreased when the output is high. As a result, it becomes possible to automatically obtain an optimum picture quality according to the brightness of the image pickup target.

However, the mere application of the AGC to the camera for picking up an image of a blood vessel does not make it possible to obtain a clear blood vessel pattern. The blood vessel pattern cannot be obtained until light of a suitable quantity is transmitted. Therefore, suitable image pickup is impossible unless the sensitivity is controlled after it is ascertained well that light for picking up an image of the blood vessel pattern is sufficiently supplied. Conversely, if the light source power is fixed without conducting light source power control at all, light continues to be added from the light sources even if intense external light is present. As a result, the saturated highlight region in the image pickup region is further aggravated, and departure from a range in which the saturated highlight region can be eliminated by the sensitivity control is also caused. It is necessary to suitably control the power of the light sources dedicated to irradiation for image pickup and the sensitivity of the camera according to the situation so as to cause a living body region to be picked up as an image to always produce a constant picture quality. Unless there is such cooperation, the power of the light sources and the sensitivity of the camera might interfere with each other in attempting a suitable picture quality and eventually convergence to a suitable picture quality might be not attained. Furthermore, in the ordinary AGC, picture quality control is exercised to optimize the picked up image as a whole. Therefore, the finger portion in the picked up image does not necessarily become optimum in picture quality. For example, when a great difference is caused in brightness between the inside of the finger and the background by external light, or when only a portion of the finger directly exposed to light from the light sources for image pickup is locally bright, the gain is set to an excessively low value by strong influence of the brightness and consequently the finger portion for which an optimum picture quality should be originally obtained becomes too dark in its image. It is also conceivable to restrict an image range in which it is determined whether the picture quality is optimum. At the time of identification, however, the finger is placed or detached. Even if the finger is placed stationarily, the finger is not always placed in the same specific position. Therefore, the brightness of the picked up image has an infinite variety according to states of the finger.

Even if external light having intensity enough to obtain the blood vessel pattern is applied to the finger, it cannot be utilized sufficiently in situations where the light source power control and the sensitivity control in the AGC or the like operate asynchronously. For example, if the AGC operates when the power of the light sources for image pickup is high and an optimum picture quality is attained, there was a possibility that the light source power could be lowered if the gain was raised. This is wasteful energy consumption. Especially in the case of energy supply using a battery or the like, the sustaining time of the battery is shortened and there is a problem from the viewpoint of preservation of the global environment as well.

SUMMARY OF THE INVENTION

An object of the present invention is to provide an image pickup scheme capable of always providing an optimum quality of a blood vessel pattern without being affected by a difference, if any, in an external environment ranging from an ordinary indoor environment to an outdoor environment in which remarkably intense external light is present.

Another object of the present invention is to actively utilize external light as one of the light sources for picking up an image of a blood vessel pattern and thereby enhance the energy saving performance.

A representative example of the present invention disclosed to achieve the objects is a personal identification apparatus including light sources for irradiating light to be transmitted by a finger, an image pickup unit for picking up an image using light transmitted by the finger, finger detection means for detecting that the finger exists in a predetermined position, finger region extraction means for extracting a region occupied by the finger from an image picked up by the image pickup unit, and gain changing means for changing an amplification factor of image pickup elements in the image pickup unit on the basis of a picture quality of a specific region within the extracted region.

To be more precise, there is disclosed a configuration including means for selecting a specific region in the gain changing means according to an output state of the light sources, and means for causing a change of an amplification factor in the gain changing means in combination with a power change of the light sources.

According to the present invention, the power control in the light sources for image pickup and the sensitivity control in the image pickup unit are adaptively combined according to the situation regardless of the external light around the identification apparatus. As a result, the finger portion in the picked up image is controlled to have an optimum picture quality. Therefore, the blood vessel pattern in the image becomes clear, and the identification precision can be improved. Furthermore, since external light is utilized as one of the light sources for image pickup, the energy consumption quantity required for the identification can be reduced.

Other objects, features and advantages of the invention will become apparent from the following description of the embodiments of the invention taken in conjunction with the accompanying drawings.

DESCRIPTION OF THE EMBODIMENTS

Hereafter, an embodiment of the present invention will be described in detail.

Figure 1:
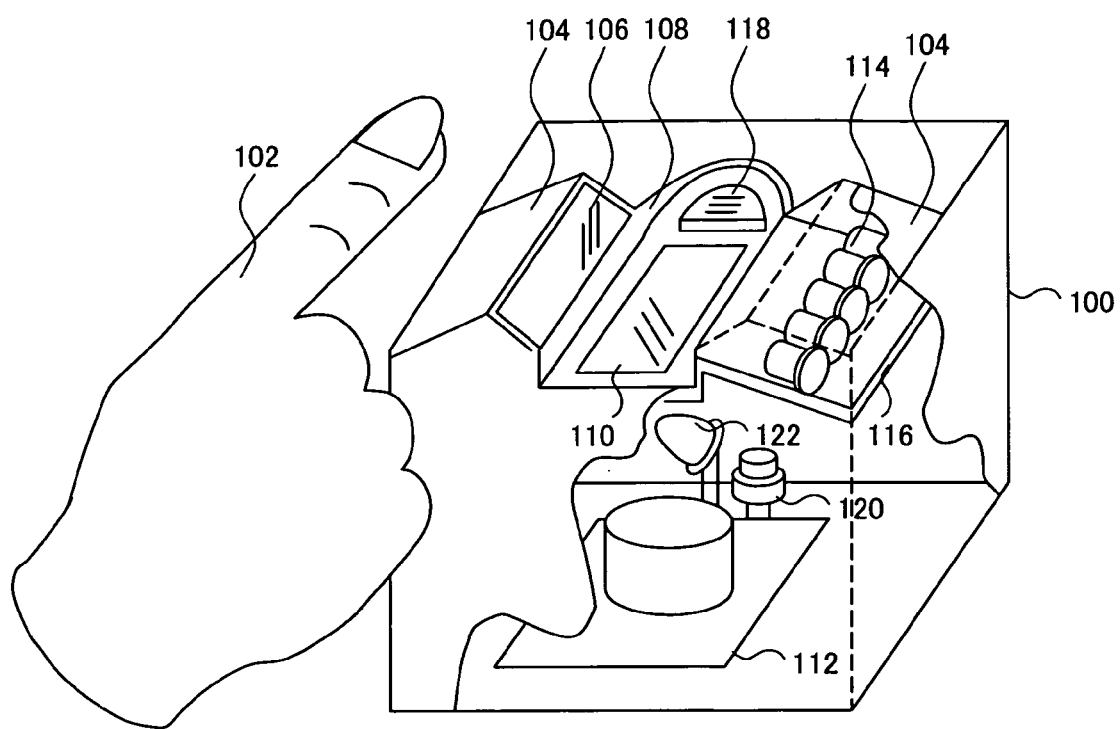
FIG. 1 shows an example of an apparatus form for implementing the present invention.

FIG. 1 is a schematic diagram of an identification apparatus 100, which implements the present invention. On a top surface of a main body, there is a guide groove 108, which exhibits a place to place a finger 102 therein in an intuitively understandable form. Light source units 104 are disposed on the left and right sides of the guide groove 108. This guide groove has a function of serving as a low light shielding wall that hides the lower half side of the finger. It is possible to physically shield external light that streams from a low position into the finger. A blood vessel pattern to be picked up as an image is present on the lower half side of the finger. When light irradiated from the left and right light sources is scattered in the finger and output from the lower side of the finger, a pattern based on the contrast between brightness and darkness is formed by a difference in light absorption quantity caused by presence/absence of a blood vessel. If at this time intense external light directly enters toward the lower half side of the finger, light emitted from the light sources and transmitted through the finger is canceled by the external light and consequently the blood vessel pattern becomes unclear. The light shielding wall prevents inflow of unnecessary external light. Since at the same time the upper part is completely opened, it is easy to place the finger in a predetermined position and it is possible to actively lead the external light to the upper half side of the finger. Because all light incident on the upper half side of the finger can be utilized as a light source for picking up an image of the blood vessel pattern on the lower half side of the finger. In this way, the apparatus has a structure that does not expose the identification apparatus as it is to the external light, but leads effective light in an easily usable form, and that can shield unnecessary light. Thus, the apparatus has a feature that the energy saving performance is enhanced by actively utilizing the external light.

Light sources 114 are disposed within the apparatus. Upper surfaces of the light sources 114 are covered. Light from each of the light sources 114 is irradiated toward the finger placed on the guide groove 108 through a light source opening unit 106. The covers disposed over the light source units also play a role of preventing light spread outside the desired irradiation direction from being reflected by a finger other than the finger to be identified or the palm and affecting the image pickup as disturbance light. When the finger is placed according to the guide groove 108, there is a button switch 118 in a position that comes in contact with the fingertip. The user can use the button switch 118 to subjectively indicate timing for conducting identification itself or exercising some control together with the identification. This switch may be a touch sensor or the like, which detects that the finger has been placed on the guide unit and controls to start predetermined processing in the identification. Conversely, if a scheme for suppressing the rejection of the person himself or herself by conducting the identification processing on a finger detected once many times in a predetermined time is adopted, the switch may not be provided. An image pickup opening unit 110 is disposed so as to correspond to a portion of the finger including the first and second joints, and the image of the finger can be picked up from a camera (image pickup unit). In general, in the blood vessel pattern of the bulb of the finger, the fingertip side is thin and unclear in many cases. Therefore, it is easier to obtain a stable identification result by conducting the identification using the above-described region. A band-pass filter for passing through only wavelengths in the near-infrared region is attached to a camera (image pickup unit) 112 to prevent light in a visible light region from affecting the picked up image and pick up an image of a blood vessel pattern clearly. The wavelength of the light sources 114 can be selected so as to contain only a component required to pick up the image of the blood vessel because they are produced artificially. On the other hand, when conducting identification using external light as a light source, it is also possible to selectively lead only light in a wavelength region effective to picking up an image of the blood vessel from external light having a wide wavelength region by using the band-pass filter and obtain wavelength characteristics similar to those of the light sources 114. As a result, it is possible to reduce the difference between the illumination condition obtained when external light is used and that obtained when the light sources 114 are used, and it becomes easier to always sustain the stable picture quality in a predetermined variation range. Light shielding partitions 116 are provided to prevent light from the light sources 114 from leaking out to the camera 112. The image pickup opening unit 110 is covered by transparent glass or acrylic board together with the light source opening units 106 to prevent a foreign substance from getting in the identification apparatus while passing through light emitted from the light sources and transmitted through the finger. It is also possible to put two functions, i.e., apparatus protection and visible light removal into one board, by using a board of an optical filter for passing through light in the infra-red region, instead of the glass or acrylic board. In addition, the cabinet inclusive of the light source opening units and the image pickup opening unit may be formed integrally using an optical filter material. An optical sensor 120, such as a photodiode or a phototransistor, having a high sensitivity in the near-infrared is disposed near the camera 112 to measure the physical intensity of light streaming into the camera. As described later, the sensitivity is controlled on the basis of a result of the measurement conducted in the optical sensor so as to make it possible for the camera to always sustain the picture quality in a predetermined range even if the intensity of the external light changes. An auxiliary light source 122 is used to detect approach of the finger without contact. The auxiliary light source 122 is disposed so as to irradiate light toward the opening unit 110.

Figure 2:
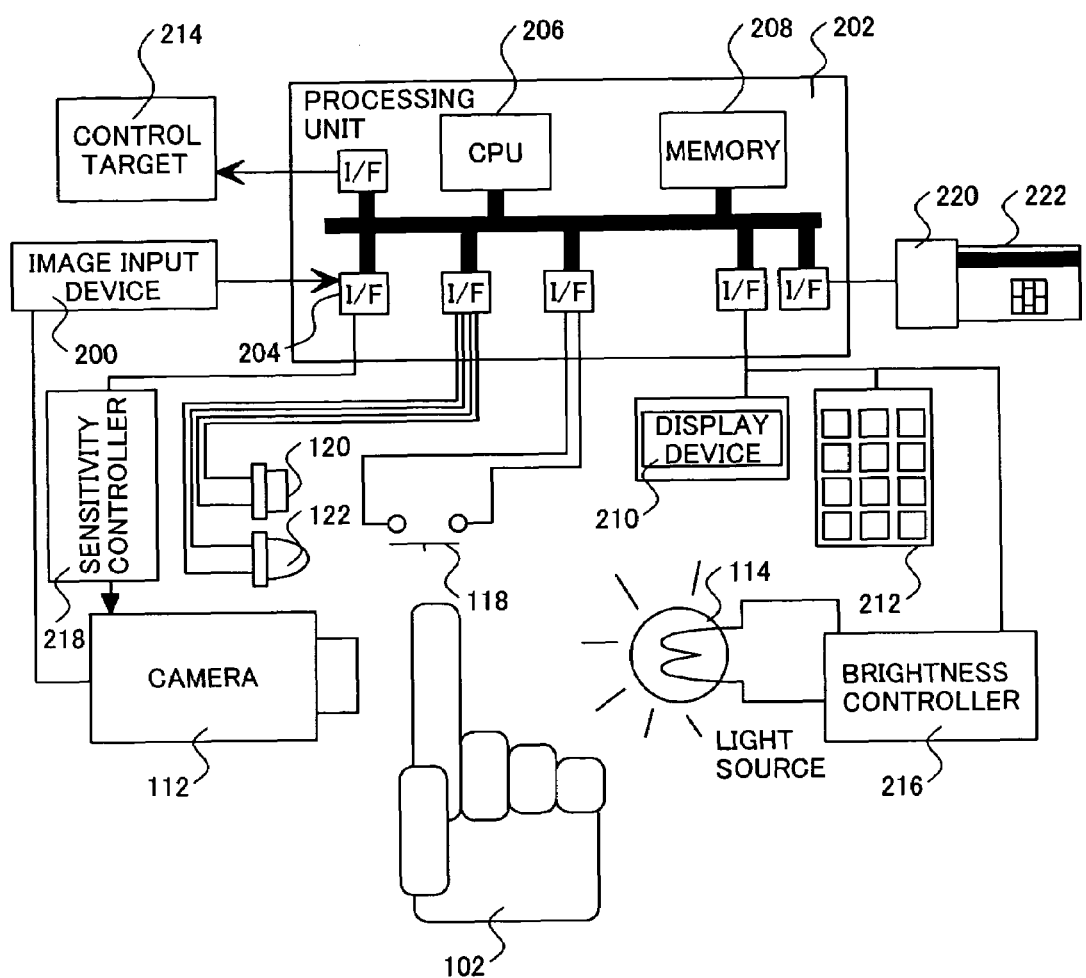
FIG. 2 shows an example of an apparatus system configuration for implementing the present invention.

FIG. 2 shows an example of a schematic block diagram of a system configuration that implements the present invention. A finger 102 is inserted in a position to which light is irradiated from the light sources 114. An image signal of a blood vessel pattern is acquired by a camera 112. The image signal from the camera 112 is converted to digital data by an image input device 200. The digital data is stored in a memory 208 via an input-output interface 204 in a computer 202. A switch 118 is also connected via an input-output interface in the same way to notify a CPU 206 of its on/off state. The CPU 206 periodically conducts processing on the image supplied from the camera to detect the finger while controlling an optical sensor 120 and an auxiliary light source 122. After the detection, the CPU 206 determines the sensitivity of the camera 112 and the optimum power of the light sources 114 so as to optimize the picture quality of the finger portion, and controls a brightness controller 216 and a sensitivity controller 218. When the optimum picture quality has been obtained, the CPU 206 extracts a blood vessel pattern and executes identification processing. And on the basis of a result of program processing, the CPU 206 exercises various kinds of control to display the result on a display device 210, send a suitable signal to a control target 214 to open/close a door, and release an immobilizer to start an engine. It is also possible to make ineffective the function of a credit card mounted on an automobile for the purpose of the ETC (Electronic Toll Collection System) for toll roads until the person himself or herself is identified. Even if an automobile is stolen, therefore, secondary damage caused by illegal purchase can be prevented. Besides them, it is also possible to cause the CPU 206 to conduct various kinds of processing according to a result of collation between an image pattern of the blood vessel picked up by the image pickup unit and registered patterns. A keyboard 212 can be used to input auxiliary information concerning the identification, such as a secret identification number. The security level can be further raised by requesting input of the secret identification number or the like. If registered images used for the identification are associated with the secret identification number, the number of the registered images used for the identification can be reduced and consequently the processing speed can be improved. As a matter of course, it is also possible to connect an external information device such as an IC card 222 via a card reader-writer 220 as occasion demands, store a registered pattern in a card that is excellent in security such as tampering resistance, and use the registered pattern. Especially in the case of an IC card, it is also possible to conduct a part or the whole of the above-described identification processing in the card. As a result, it becomes unnecessary to put out the registered patterns to the outside of the card, and consequently the security can be further enhanced from the viewpoint of personal information protection.

Figure 3:
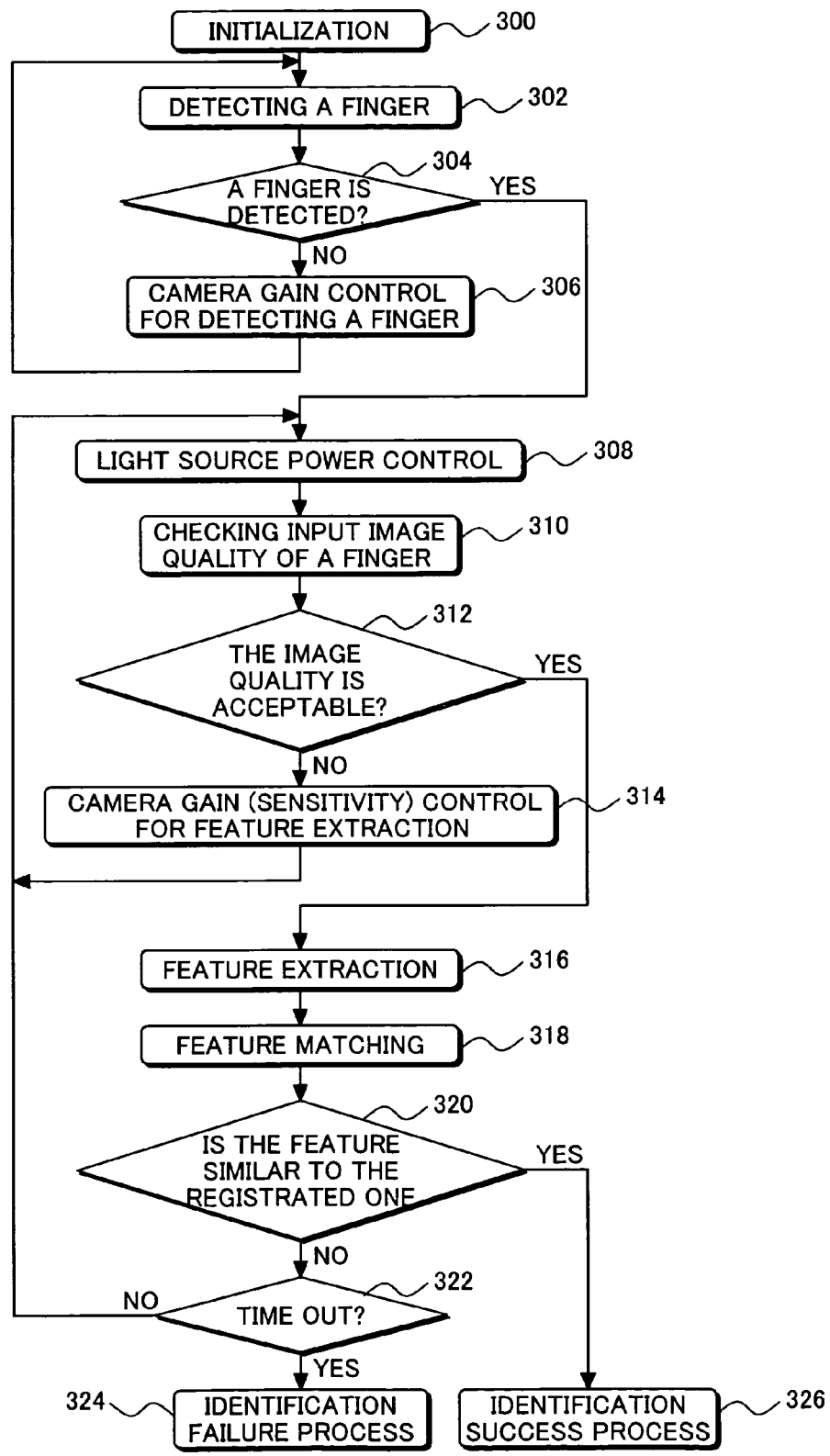
FIG. 3 shows an example of a software flow for implementing the present invention.

FIG. 3 shows an example of a software flow executed by the hardware, particularly the CPU 206. In a process 300, an initial value is substituted into a temporary variable required for initialization of the whole program and program execution. If a shift to the initial state is completed, it is detected on the basis of an image input from the camera 112 whether a finger has been inserted (302). Here, detection is conducted on the basis of the image without using a touch sensor such as a button switch. At a stage in which the finger does not arrive at a predetermined position in the apparatus, therefore, the finger can be detected earlier. As a result, the start time of the sensitivity and light source power control can be made earlier. When the finger has arrived at a predetermined position, a smooth shift to feature extraction processing can be conducted in the state where optimum parameters have been set. Thus the identification response time felt by the user can be shortened. As a matter of course, a configuration in which the identification is started by touching the button switch 118 may also be used.

For detecting the finger by conducting image processing on the basis of the camera image, basically it is necessary only to detect a temporal image change between the case where the finger is present and the case where the finger is not present. Therefore, the auxiliary light source 122 serving as a light source for finger detection is provided, and the finger is detected by a change in an image picked up by using light from the auxiliary light source 122.

In particular, if the auxiliary light source 122 is set to irradiate light from the predetermined position in which the finger should be placed, to a space over the position, an image change can be made more conspicuous. If the finger approaches the predetermined position, the finger is illuminated bright by the irradiated light. If the finger is not present or the finger is distant, the light does not arrive at the camera and consequently a dark image is picked up. That is the reason why the image change can be made more conspicuous. In addition, if the auxiliary light source 122 is turned on and off, presence of the finger causes the following change to appear clearly. In other words, when the auxiliary light source 122 is on, a region illuminated brightly is found in a picked up image. On the other hand, when the auxiliary light source 122 is off, the region becomes dark. If the finger is not present or the finger is distant, the image remains dark and there is little change, regardless of whether the auxiliary light source 122 is on or off. By utilizing this, the finger can be detected with relatively high precision. By the way, the light sources 114 for picking up an image of the blood vessel pattern can be used for finger detection as well, resulting in a reduced component cost. On the other hand, the light direction of the light sources 114 must be set so as to illuminate the finger optimally when the finger is placed in the predetermined position. Therefore, a change in the image caused by emission of light is hard to occur until the finger arrives at the predetermined position. On the way of the finger approaching the predetermined position, reaction is not caused. Therefore, detection of the finger is delayed, and the processing time felt by the user becomes long. By separately providing the auxiliary light source and irradiating light toward a place where the finger passes through before it arrives at the predetermined position, it becomes possible to detect the finger at an earlier point in time. If the image pickup range of the camera is exposed to intense external light in the situation where the light source for finger detection is set and the camera has been controlled to have a sensitivity capable of detecting a minute difference between brightness and darkness, there is a fear of producing an image including a saturated highlight region in which the luminance is always saturated at a maximum value regardless of whether the finger is present and whether the auxiliary light source is on. In this state, an image change according to the presence/absence of the finger is not generated. On the other hand, if the gain is lowered excessively, a saturated shadow image in which the luminance becomes always the minimum value is obtained regardless of whether the finger is present and whether the auxiliary light source is on. Eventually, an image change according to the presence/absence of the finger is not obtained. In the present embodiment, therefore, a configuration for finding a gain value suitable for the environment, such as irradiation of external light, in which the apparatus is placed is also provided and the gain control of the camera is conducted (306).

For obtaining the gain value, the optical sensor 120 disposed in close vicinity to the camera is used in the present invention. A physical absolute quantity of light that streams into the camera via the optical sensor is found, and a gain value optimum for the finger detection is calculated on the basis of the absolute quantity. Specifically, a circuit is formed using elements, such as photodiodes or phototransistors, having electrical characteristics that change according to the light intensity. And a change of an output voltage of the circuit is converted to a digital value by an A-D converter, and the digital value is taken into the CPU as data. The CPU finds a gain value to be set, using a look-up table or a predetermined function expression, on the basis of the data, and conducts setting for the camera. As a result, the optimum gain value can be found instantaneously. At this time, the CPU controls timing so as to conduct gain setting only when the auxiliary light source is off. Because light from the auxiliary light source 122 affects the optical sensor 120 and a correct external light state cannot be acquired when the auxiliary light is on. Unlike the ordinary AGC function, a relation expression between the output data of the optical sensor and the gain setting value is found on the basis of whether the image change caused by the presence/absence of the finger becomes the maximum, instead of the superiority or inferiority in picture quality. This aims at facilitating the image acquisition of the finger.

For searching for a suitable gain value while judging the image, it becomes necessary to verify several images to attain convergence to an optimum value. If a change such as going in and out of the finger occurs during that time, there is a possibility that it will not be able to find a suitable gain value. According to the above-described configuration of the present invention, however, the setting time is short and there isn't such a fear.

As another embodiment for detecting the finger, the output value of the optical sensor can be used as it is. If external light streaming into the camera is intense, the output value of the optical sensor remarkably changes according to whether the finger is not present and light comes in directly, or the finger is held up and the finger shields direct irradiation like an umbrella. This change is utilized for finger detection. As a matter of course, it is desirable to use the change of the output value obtained only when the auxiliary light source is off, at this time as well. When the external light is weak, however, the finger detection using the image is more suitable, because a change in quantity of light incident on the optical sensor caused by the presence/absence of the finger is small and consequently it is difficult to discriminate a change in the output value of the sensor from an illumination change in the surroundings.

It is also possible to use the finger detection method utilizing the sensor and the finger detection method utilizing the camera image by combining them with each other. For example, if the sensitivity of the camera cannot be completely controlled to become sufficiently low under intense external light, approach of the finger cannot be detected using the image. However, the approach of the finger can be detected by detecting a change with the sensor. By exercising control again to lower the sensitivity on the basis of the detection, modification can also be conducted so as to make it possible to pick up an image of the finger precisely.

In the above described example, the optical sensor is disposed separately from the image pickup elements. Alternatively, it is also possible to use the output itself of the image pickup elements (112) such as a CCD. In this case, the function of the optical sensor can be substituted for to some degree by newly installing a route by which the absolute value of the light intensity can be acquired regardless of the gain that has been set for the image pickup elements. As a result, it is not necessary to provide a new sensor, resulting in a reduced cost. In addition, if there is a margin in the processing time, a method of taking in an image with a gain of 0, i.e., that is not amplified at all, in the intervals of image taking in for identification and calculating information corresponding to the output value of the optical sensor on the basis of this image is also conceivable. According to this method, the interval of taking in the image for identification becomes long, but a new hardware configuration becomes unnecessary.

If the finger is detected correctly by the gain control (304), subsequently picture quality control is exercised so as to obtain blood vessel pattern most clearly, by suitably combining two modes, i.e., a mode A for controlling the power of the light sources 114 (308) and a mode B for controlling the sensitivity of the camera (314) according to the situation. Specifically, the control is exercised in the following two stages. First, the sensitivity of the camera is kept sufficiently high, and picture quality control using the mode A is exercised preferentially (308). If the light quantity is too large and a sufficient picture quality cannot be obtained even when the power of the light sources 114 is set to 0 (310 to 312), the sensitivity of the camera is controlled (314). Owing to such priority assignment, it is possible to obtain a clear image of the blood vessel pattern by transmitting a sufficient quantity of light through the finger. At the same time, the sensitivity of the camera is prevented from being lowered than needed, and consequently noise is prevented from being easily superposed on the image. In addition, since the intensity of the light sources to be supplied to provide the same picture quality can be held down, the electric power can be saved. If an optimum picture quality is obtained by exercising the above-described controls, a feature extraction (316) is conducted using the obtained image, and collation of an obtained feature pattern with previously registered feature patterns (318) is conducted. If the obtained feature pattern coincides with a registered feature pattern (320), the processing proceeds to an identification success process 326 and corresponding processing such as unlocking is conducted. In the case of non-coincidence, the processing returns to 308 and the processing beginning with the picture quality control is repeated. In addition, time elapse from the detection of the finger is measured. If the identification has not succeeded within a predetermined time (322), the processing proceeds to an identification failure process 324, in which corresponding processing such as alarm issuing may be conducted. When processing is not conducted normally, therefore, it becomes possible to cope with this separately.

Hereafter, details of the picture quality control will be described. First, the gain of the camera optimized for the finger detection is altered to that for feature extraction. Since the finger has been already detected at this point in time, it can be premised that the finger is present certainly. Therefore, the gain is controlled so as to cause a region in an image that should emit intense reflected light because of existence of the finger and light irradiated from the auxiliary light source to have predetermined brightness when the auxiliary light source 122 is on and cause the same region to have predetermined darkness when the auxiliary light source 122 is off. This is the initial state of control.

Figure 4:
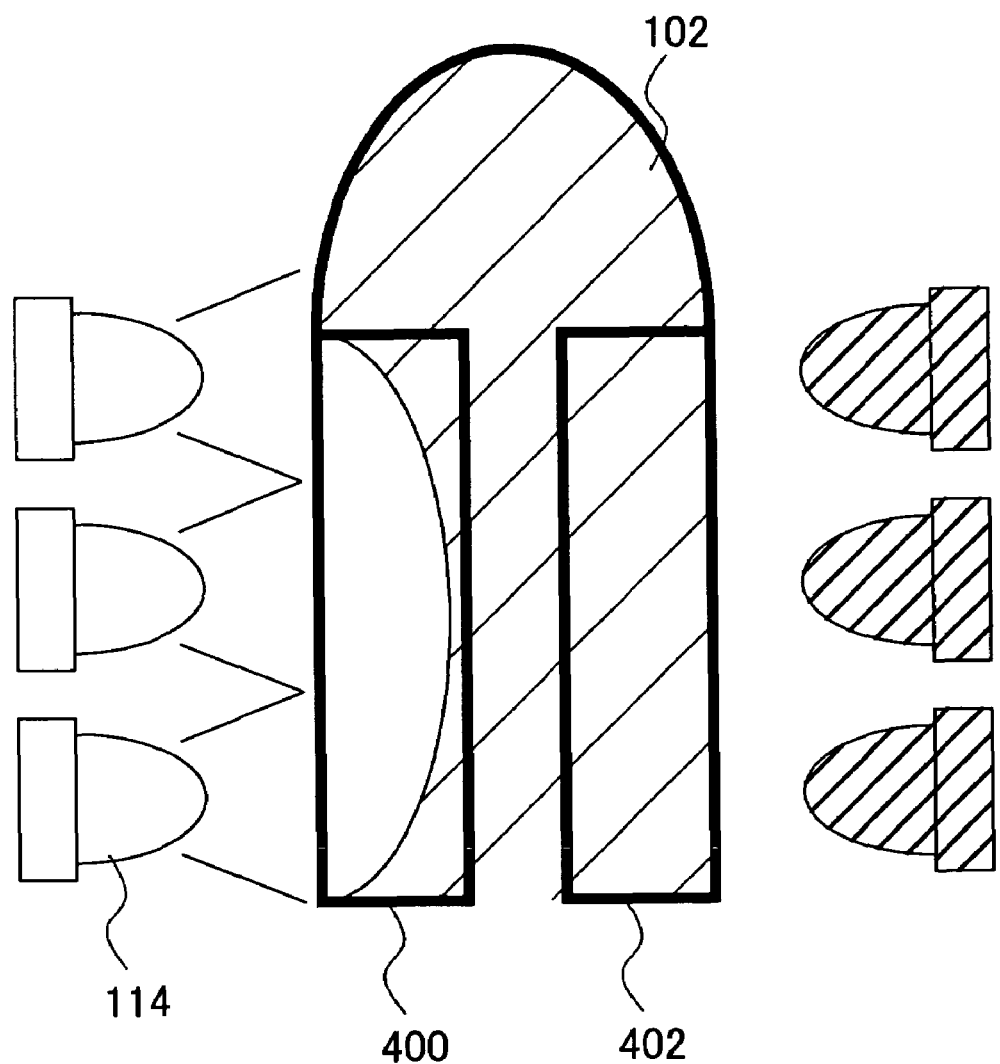
FIG. 4 shows an example of an optimum region for making a picture quality decision of a finger.

As for the finger identification apparatus of the open type shown in FIG. 1, a light source power control method for obtaining a clear image of the blood vessel pattern of the finger under external light is described in US2004/0184641. Basically, the light sources disposed on the left and right sides of the finger are set so as to cause the left light sources to become intense and the right light sources to become weak, and an image is acquired. Conversely, an image is acquired with the left light sources caused to become intense and the right light sources caused to become weak. Thus, two images are picked up. A left half and a right half are selected respectively from the two images, and combined. Even if a saturated highlight region occurs in a half of each picked up image located near the intense light sources, the remaining half has a clear image. Therefore, an image that is clear as a whole is obtained by combining clear half images. FIG. 4 shows an example in which the left light sources 114 are on and the right light sources are off. In a region 400 that is the left side of the finger 102, a region including a saturated highlight region occurs. As the location advances to the right, the brightness becomes dark. In the right half, a saturated highlight region is not present. However, there is difference in finger among individuals. Even under the same light source power, therefore, the brightness of the half that is not located on the light source side becomes insufficient in the case of a thick finger, and the brightness becomes excessive in the case of a thin finger. Such a problem is eliminated by controlling the outputs of the light sources.

In the case where intense external light is irradiated to the finger, the external light plays the same role as the light sources, resulting in a state resembling the state in which the light sources are on. Even if one of the left and right light sources is completely off, a saturated highlight region occurs even in a half opposite to the light sources turned on according to the intensity or way of striking of external light, and it becomes difficult to extract the blood vessel pattern. In the present embodiment, therefore, the picture quality is improved by adaptively combining and controlling the light source power and sensitivity of the camera. In the control, it is necessary to exercise feedback control between the picture quality of the picked up image and the preset light source power value. If the whole of the picked up image is designated as the subject of picture quality, however, the finger portion is not controlled to have a correct picture quality under the influence of brightness of the background portion other than the finger. Therefore, a region occupied by the finger is extracted from the image, and only the region is designated as the subject of picture quality (310). First, therefore, a contour line of the finger is extracted by conducting image processing on the image picked up by the camera 112. As to the contour extraction, various conventional techniques are known, and consequently they will not be mentioned in detail. In the inside of the extracted contour line, a region 402 on the side remote from light sources that are on is designated as the subject of the picture quality decision. In other words, the place where the light from the light sources that are on is most hard to reach is selected. Specifically, it is desirable to select a region located near an area between a middle line drawn between a center line of the finger and the contour line, and the contour line. The tip and the root of the finger are remote from the light sources, and light does not arrive at them in some cases. If a region obtained by excluding regions near the tip and the root of the finger is utilized, therefore, it is easy to obtain desired performance. The reason why the vicinity of the contour is selected will now be described. In the vicinity of the finger, the thickness of the finger is thin and the quantity of external light lost when the external light is transmitted through the finger is little. If the external light is intense, therefore, a saturated highlight region first occurs in the vicinity of the contour and a problem in the blood vessel pattern tends to occur in the vicinity of the contour. For this reason, the vicinity of the contour is selected. If a saturated highlight region occurs in the region 402, it is meant that the external light is intense and consequently the power of the light sources that are on is first lowered. And the mode (mode B) for preferentially controlling the sensitivity of the camera is entered.

Figure 6:
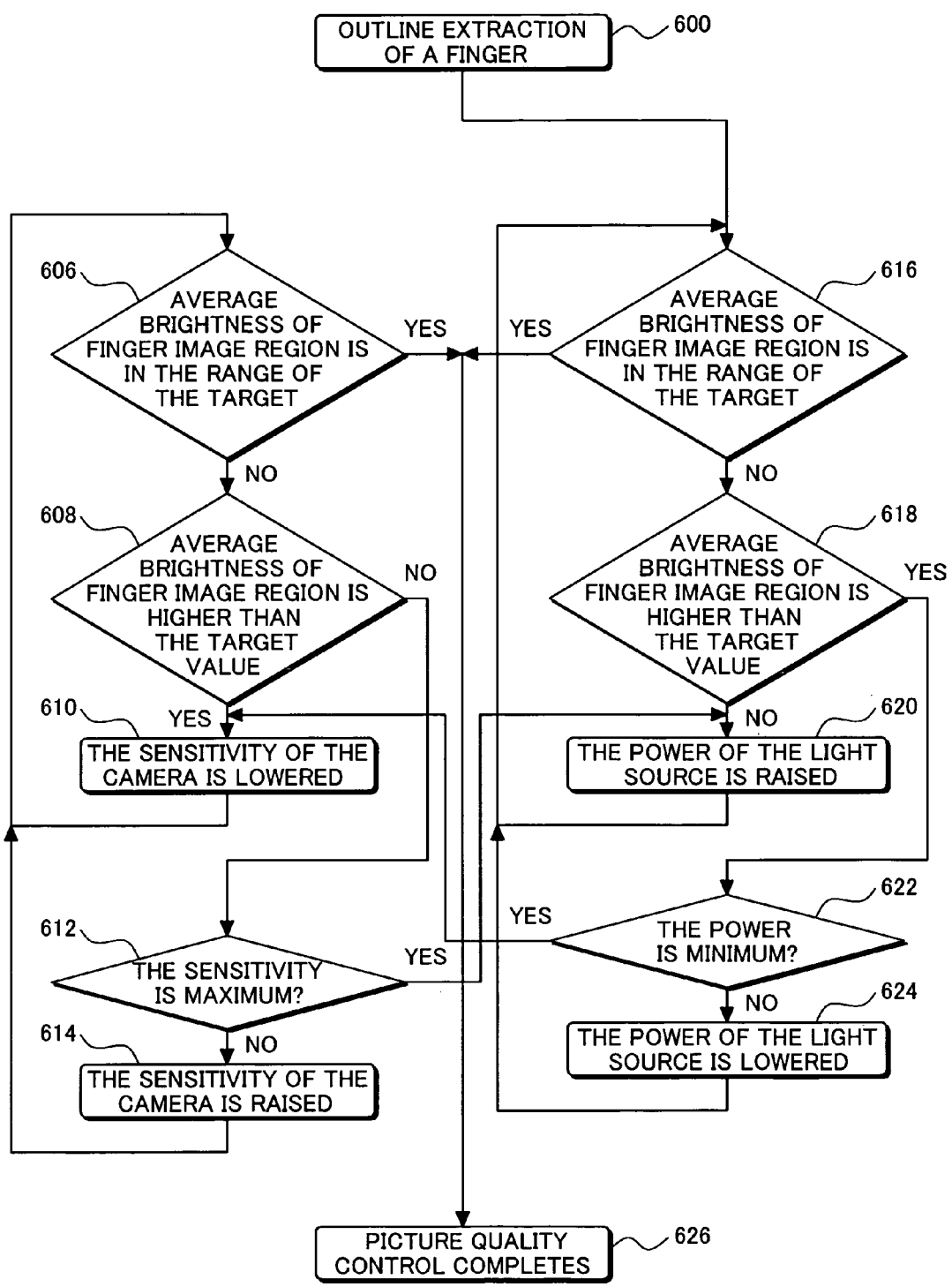
FIG. 6 shows an example of a flowchart showing a part of the flow shown in FIG. 3, in more detail.

FIG. 6 is a flowchart specifically showing this processing. FIG. 6 shows an example of details of 308 to 314 shown in FIG. 3. First, the contour of the finger is extracted, and a region inside the finger is determined (600). And basically, a shift to the mode (mode A) for preferentially controlling the light source power is conducted, and the processing proceeds to a process 616. If a saturated highlight region is seen inside the finger on the side of the light sources that are off although the light sources on the side are off, or the output value of the optical sensor 120 indicates that external light is intense, then it is meant that the influence of external light is obviously strong. In such a case, it is possible to set the light source power to a lowest value that can be set, make a shift to the camera sensitivity control mode, and proceed to the side of a process 606. By preparing such a short-circuit route, the picture quality control can be exercised at high speed. In the case where an optical sensor is used, the convergence speed of the picture quality control is further raised by, for example, supposing a parameter that indicates whether the external light is intense, according to the output value of the optical sensor, and exercising control.

In the light source power control mode beginning with the process 616, the light source output is controlled so as to optimize the picked up image according to the above-described light source power control technique. First, as described above as the process 310, it is checked whether average brightness of the finger image region 402 is in a target range (616). If the average brightness is lower than the target (618), the light source power is raised (620). If the average brightness is higher than the target (618), it is checked whether the light source power can be further lowered (622). If possible, the light source power is lowered (624). If a saturated highlight region is seen, or more specifically pixels having the saturated luminance are seen collectively near the contour line of the finger even when the light source power is set to its lowest output, a shift to the sensitivity control mode is conducted and then the sensitivity of the camera is further lowered (610).

In the camera sensitivity control mode, the method described as the process 310 is used in the same way as the light source power control mode. It is checked whether average brightness of the finger image region (402) on the side opposite to the light sources that are on is in the range of the target (606). If the average brightness is higher than the target (608), the sensitivity of the camera is lowered (610). If the average brightness is lower than the target, it is checked whether the sensitivity can be further raised (612). If possible, the sensitivity is raised (614). If the target value is not yet reached although the sensitivity of the camera is set to a highest value that can be set, there is a limit in the image pickup using the sensitivity control alone. Therefore, the light source power is raised (620), and a shift to the light source control mode is conducted.

In the above-described flow, the upper limit is provided in the sensitivity control range of the camera. If the upper limit is exceeded, a shift to the light source power control is conducted. This is a contrivance for ensuring the picture quality. It is possible to attain the average luminance that is nearly equal to that obtained by raising the light source power, by raising the sensitivity of the camera. If at the same average luminance the case where the light source power is raised is compared with the case where the sensitivity of the camera is raised, a higher picture quality is frequently obtained in the case where the light source power is raised. Because noise caused in the picked up image is obviously less when picking up an image using sufficient light moderately as compared with when amplifying less light and picking an image. This is one reason why the processing proceeds from the process 600 in the flow preferentially to the process 616 in the light source power control mode.

In addition, there may be a case where the sensitivity is set to a very low value at the time of, for example, initial state setting after the finger detection and the light source power is insufficient even if it is maximized. In this case, it is also possible to cope with this by further providing a step for shifting from 620 to 612. In the same way, there may also be a case where the range of the target is not yet arrived at even if the light source power is maximized, because of the upper limit provided in the sensitivity control range. For that case as well, a new route may be provided as hereafter described. In the light source power control mode, it is ascertained that the target is not reached even if the light source power is maximized. In addition, the upper limit of the sensitivity control range of the camera is temporarily raised to an upper limit that can be mechanically set as the camera, or an upper limit at which degradation in picture quality caused by noise incurred at the time of high sensitivity image pickup does not exert a bad influence on identification precision. Then, a shift to the sensitivity control mode is conducted. As a result, the control range of the picture quality can be expanded so as to include the difference among individuals such as a finger that does not transmit light easily. The processing heretofore described is repeated. When the brightness of the finger has come in the range of the target, the picture quality control is finished (626).

If a necessary and sufficient quantity of light is supplied to the finger by the flow, external light is preferentially used as the light source for image pickup and it becomes possible to reduce the energy consumption in the light sources. As for the method for controlling the sensitivity of the camera, there is also a method of controlling the exposure time of the image pickup elements, besides the method of controlling the gain for the output of the image pickup elements. If a lens can be controlled, the iris may also be controlled optically.

In the foregoing description, it has been supposed that the light sources on the left side shown in FIG. 4 are on. Conversely, if the light sources on the left side are off and the light sources on the right side are on, processing similar to that described above is conducted by regarding the region 400 as the subject of the picture quality decision. As a result, it is possible to always pick up an image of the finger with an optimum picture quality without depending upon the intensity of external light, and a clear blood vessel pattern is obtained. By the way, if the sensitivity of the camera is sufficiently high and the necessary and sufficient quantity of external light is present, it is also possible to acquire the blood vessel pattern by exercising the sensitivity control alone of the camera without using the light sources 114 at all. If use in an environment where external light is always irradiated is considered, a configuration that does not incorporate the light sources 114 in the apparatus from the beginning is also possible. For example, in an environment where an intense spot light is always applied to the identification apparatus, such a way to use is also possible.

Figure 5:
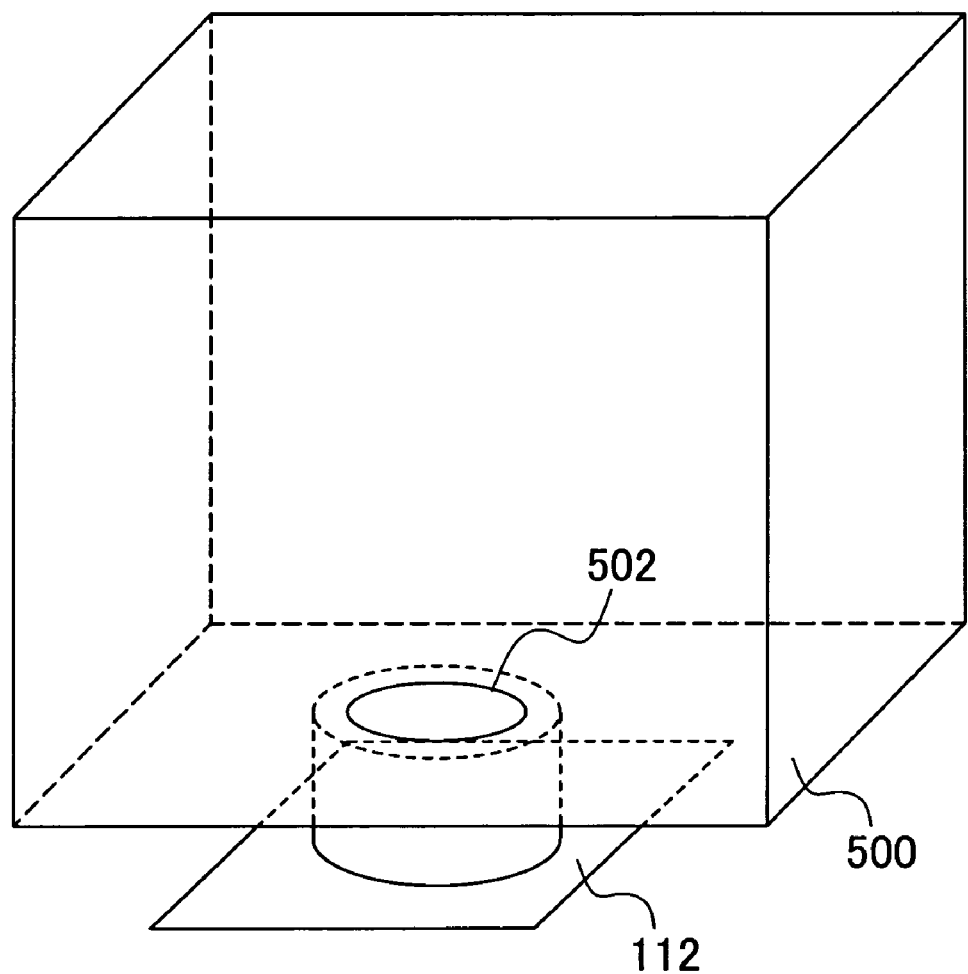
FIG. 5 shows an example of a structure for preventing reflection within the apparatus.

If external light streaming into the camera unit is intense, there is a fear that the external light reflected by an internal mechanical component in the internal configuration of the apparatus shown in FIG. 1 will pose a problem in the feature extraction. For example, as for external light streaming from the opening 110, light reflected by the tip of the lens barrel of the camera and returned to the finger is different in surface reflectance of mechanical components and optical path length from light reflected by the bottom of the camera and returned to the finger. Therefore, a difference between brightness and darkness occurs and a light pattern is generated on the finger. Since this pattern is similar to the blood vessel pattern, this pattern is included in the extracted pattern. As a result, the extracted pattern becomes different from the blood vessel pattern registered under the ordinary external light, resulting in an identification failure. FIG. 5 shows an example in which a partition 500 is provided within the apparatus 100 between the opening 100 and the camera. The partition 500 excludes internal mechanical components other than the opening 110 and the opening of the camera from a space surrounded by the partition. Owing to the smooth surface shape free of differences in level and projections, it is possible to prevent a pattern from being generated by reflection of external light. In the present embodiment, the opening (lens) of the camera is stuck to a hole 502 formed through the partition so as to have a size just enough to pick up an image of a necessary portion of the finger, without differences in level. In addition, the inside of the partition is covered by a material or paint that absorbs near-infrared light to suppress the reflection itself. Differences in level similar to annual rings are provided in the barrel of the lens in some cases for a reason such as enhancing the light-gathering performance. Since these differences in level cause a pattern between brightness and darkness, however, it is desirable that these differences in level are not provided. In addition, it is more desirable to provide coating using a material or paint having a high infrared light absorption property, in the lens as well.

Figure 7:
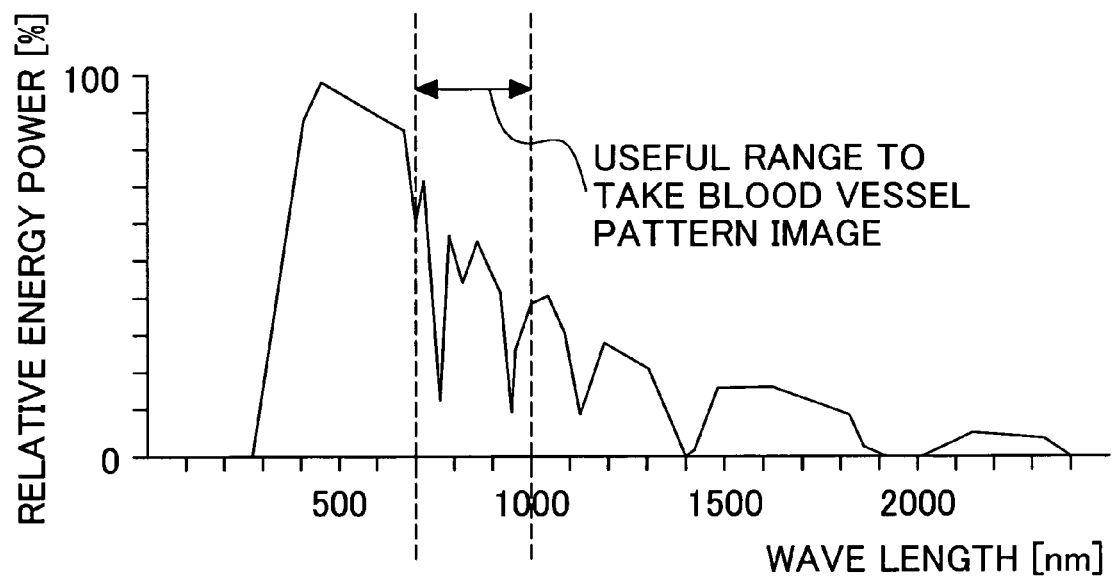
FIG. 7 is a graph showing relative energy power of sunlight as a function of its wavelength.

The energy intensity of sunlight is very high. In some cases, therefore, the range of optical energy that can be accepted by the camera is exceeded, and even the sensitivity control cannot be exercised. FIG. 7 is a graph nearly representing the energy intensity of sunlight at the ground surface every wavelength. However, it is appreciated that energy is scattered over various wavelengths. A wavelength range required to pick up an image of a blood vessel pattern is limited between 700 nm and 1000 nm. A living body tissue transmits well only light in this wavelength region, and hemoglobin in blood absorbs well light in this wavelength region. Therefore, differences between the blood vessel portion and other living body tissues are imaged clearly. As a result, the blood vessel pattern is formed. Therefore, the total quantity of energy incident on the camera can be decreased by attaching a band pass filter that passes through only the wavelength range to the camera. Even if the bandwidth is limited, the energy quantity in the necessary wavelength region is not changed and consequently the picture quality is not degraded. As the band is narrowed down, the total quantity of energy is decreased. However, it is necessary that identification can be conducted even in an environment where external light is not present and it is very dark. At that time, it is necessary to pick up an image with the light sources turned on. Therefore, it is desirable to set the band of the filter so as not to cut the effective wavelength region of the light sources, especially the wavelength region having high energy intensities. As a result, the all-round sensitivity control becomes possible whether it be under intense sunlight or on a dark night.

Figure 8:
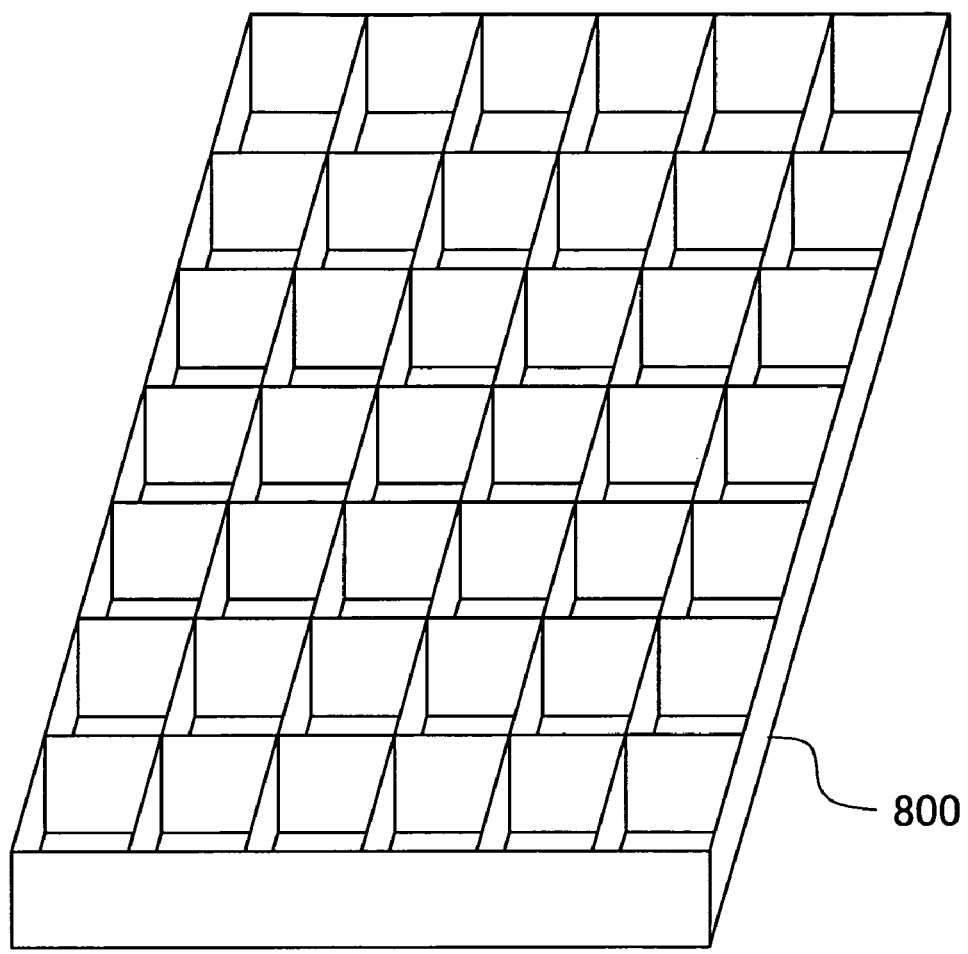
FIG. 8 shows an example of a filter for preventing entry of external light from an oblique direction.

FIG. 8 shows an example of a different filter for suppressing the influence of intense external light. This filter has a shape in which partition plates are provided in a box in a grid form. In FIG. 8, very large and high grids are shown. By providing the filter with a shape formed by arranging a large number of minute grids that are indiscernible to the naked eye, however, it is possible to prevent grid lines from being imaged in the picked up image as they are. Owing to the existence of the grid-like plates, it is possible to pass through only light perpendicular to the filter and cut light in an oblique direction. By mounting this filter between the camera and the finger, it becomes possible to pass through only light for picking up an image of the blood vessel pattern emitted from the finger and prevent external light, such as light in the oblique direction and light reflected in the apparatus, from arriving at the camera. As the present filter, a film that is the same, in principle, as the film used to prevent the screen of the portable telephone from being watched from the flank can be used, and it is easily available.

Figure 9:
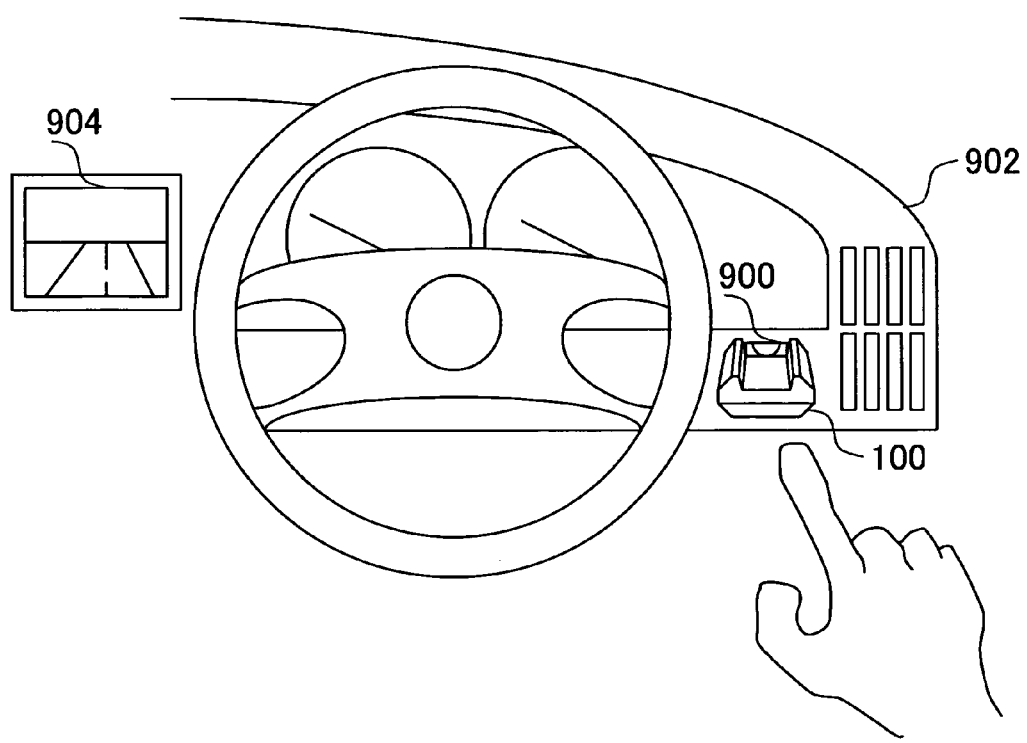
FIG. 9 shows an example of an identification apparatus according to the present invention attached to an instrument panel of an automobile.

FIG. 9 shows an example in which the present apparatus 100 is attached to an instrument panel 902 of an automobile. An engine start button 900 is used as the blood vessel identification start button 118 as well. With an operation for ordering the engine start, identification of the person himself or herself can be conducted. If the identification is successful, the immobilizer is canceled and the engine is started. If the identification is unsuccessful, the engine is not started. Since the identification can be conducted in the natural operation for the engine start, the burden imposed on the user is also lightened. When conducting mobile commerce, such as receiving service or purchasing commodities, via a communication network in cooperation with a car navigation system 904, it is also possible to use the present apparatus as the identification means for conducting settlement of accounts more safely and certainly. For example, identification is conducted by holding up a finger over the present apparatus instead of the conventional inputting of a secret identification number. As a way of cooperation, it is also possible to display guidance for the identification method of the present apparatus by using the screen of the car navigation system.

Figure 10:
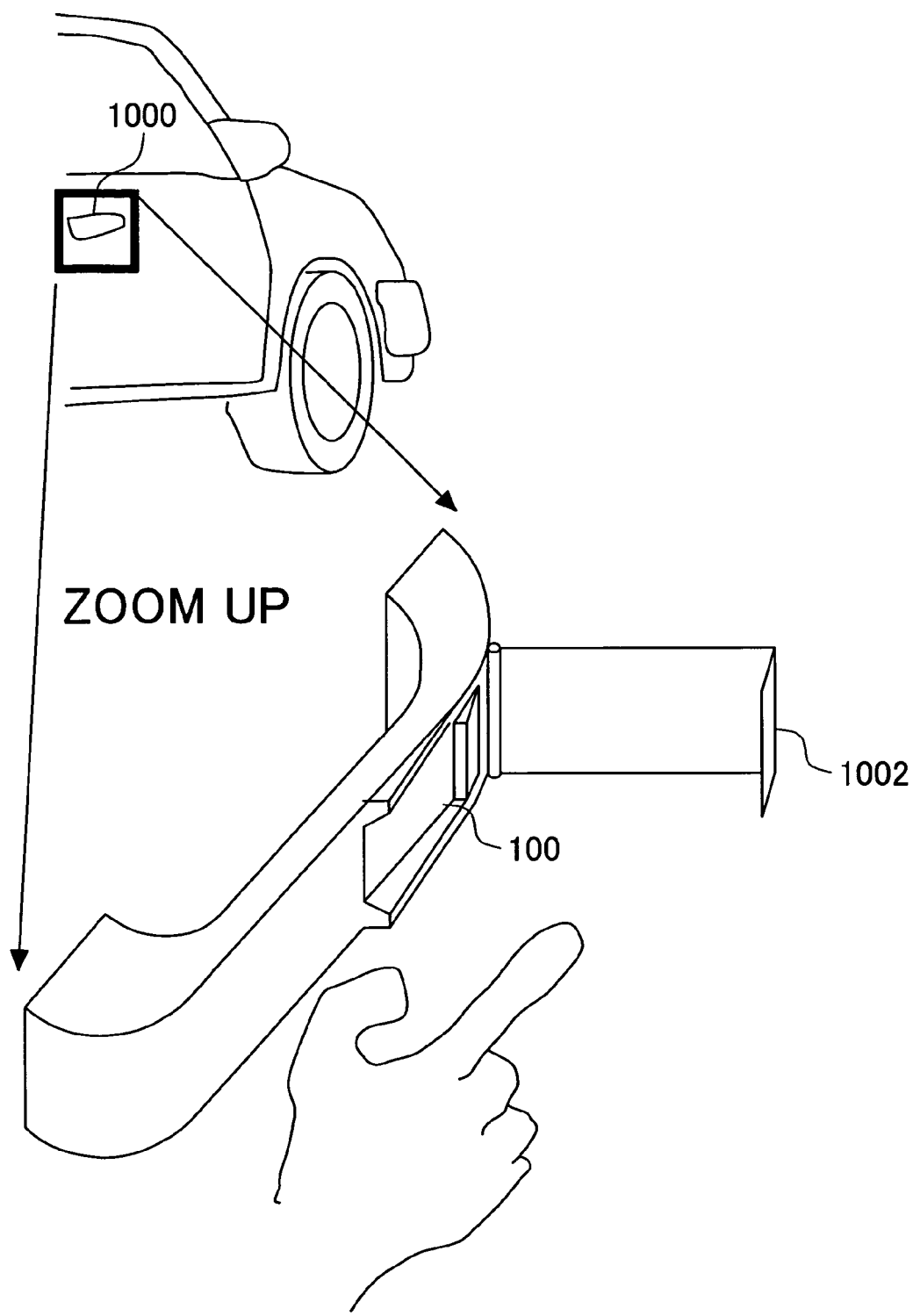
FIG. 10 shows an example of an identification apparatus according to the present invention attached to a door handle of an automobile.

FIG. 10 shows an example in which the present apparatus 100 is attached to a door handle 1000 of an automobile. When opening the door, the door is unlocked by conducting the blood vessel identification using the present apparatus. The identification start button 118 is used as a door lock button as well. When locking the door, the door is locked by pressing the button 118. In the case of locking, it is not necessary to especially conduct the identification of the person himself or herself from the viewpoint of security. Therefore, the locking may be conducted by only pressing the button 118 even if the identification is unsuccessful. In alternative implementation, the button 118 is pressed in a correctly identifiable form. If the identification of the person himself or herself is successful, the data is stored together with ordinary registered data as one of latest registered data. The stored data can be handled as registered data to be referred to when unlocking the next time. Even in an unstable environment where an obtained feature tends to differ from that obtained at the time of registration because of, an environment of the automobile, an extreme change in the health state, an injury, or a change in the way of placing the finger, therefore, the safety of the identification can be improved because the latest data can also be referred to. Furthermore, a cover 1002 can also be attached to the identification apparatus. Even if the automobile is placed outdoors and tends to be weather-beaten, it is possible to prevent dirt or dust from damaging the apparatus and making the identification unstable.

The identification apparatus has heretofore been described by taking a finger blood vessel identification apparatus of open type taking a shape that can take in external light most easily, as an example. However, it is a matter of course that the above-described technique for implementing the stabilization of the picture quality of picked up image and reduction of the energy consumption in the light sources by exercising the power control of light sources for image pickup and the sensitivity control of the image pickup system synthetically can be applied to finger blood vessel identification apparatuses having a different form and other biometric schemes in which an image of a living body is picked up using light to conduct personal identification.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A personal identification apparatus comprising:
   an image pickup unit for picking up an image by using light transmitted by a finger; and
   a processing unit for conducting personal identification by extracting blood vessels from an image picked up by said image pickup unit,
   wherein:
   said processing unit detects that the finger exists in a predetermined position, and extracts a region occupied by the finger from the picked up image, and
   said processing unit controls a light source power control unit for changing power of light sources and/or a sensitivity control unit for changing an amplification factor of image pickup elements in said image pickup unit, on a basis of information in the extracted region.

2. The personal identification apparatus according to claim 1, wherein:
   said processing unit determines whether a quantity of light irradiated to the finger is within a predetermined range, on a basis of the information in the extracted region,
   when the quantity of light irradiated to the finger is judged to be outside the predetermined range, said processing unit determines whether the quantity of light irradiated to the finger can be caused to be within the predetermined range by controlling the light source power control unit, and
   when it is judged that the quantity of light irradiated to the finger cannot be caused to be within the predetermined range, said processing unit controls the sensitivity control unit.

3. The personal identification apparatus according to claim 2, wherein:
   when the quantity of light irradiated to the finger is judged to be larger than the predetermined range, said processing unit lowers power of the light sources via the light source power control unit, and
   when the quantity of light irradiated to the finger is judged to be smaller than the predetermined range, said processing unit raises power of the light sources via the light source power control unit.

4. The personal identification apparatus according to claim 2, wherein:
   said processing unit detects existence of the finger on a basis of a change of the image picked up by a camera with time.

5. The personal identification apparatus according to claim 2, further comprising an optical sensor,
   wherein said processing unit calculates a gain value on a basis of a result of measurement conducted using said optical sensor, controls a sensitivity of said image pickup unit via the sensitivity control unit so as to attain the gain value, and conducts the finger detection.

6. The personal identification apparatus according to claim 1, wherein:
   when the quantity of light irradiated to the finger is judged to be larger than the predetermined range, said processing unit lowers power of the light sources via the light source power control unit, and
   when the quantity of light irradiated to the finger is judged to be smaller than the predetermined range, said processing unit raises power of the light sources via the light source power control unit.

7. The personal identification apparatus according to claim 6, wherein:
   when the quantity of light irradiated to the finger is judged to be large even if the power of the light sources is minimized, or when the quantity of light irradiated to the finger is judged to be small even if the power of the light sources is maximized, said processing unit controls a sensitivity of said image pickup unit via the sensitivity control unit.

8. The personal identification apparatus according to claim 1, wherein:
   the light sources irradiate light to the finger alternately from left and right directions, and
   said processing unit uses information in a partial region located on a side of light sources that are off, in the extracted region.

9. The personal identification apparatus according to claim 1, wherein:
   said processing unit detects existence of the finger on a basis of a change of the image picked up by a camera with time.

10. The personal identification apparatus according to claim 9, further comprising an auxiliary light source,
    wherein said processing unit detects existence of the finger on a basis of an image picked up using light irradiated by said auxiliary light source.

11. The personal identification apparatus according to claim 1, further comprising an optical sensor,
    wherein said processing unit calculates a gain value on a basis of a result of measurement conducted using said optical sensor, controls a sensitivity of said image pickup unit via the sensitivity control unit so as to attain the gain value, and conducts the finger detection.

12. The personal identification apparatus according to claim 1, wherein:
    an opening provided between the finger and the camera, and an opening of the camera are surrounded by a partition formed of smooth surfaces, and
    other internal components are provided outside the partition.

13. The personal identification apparatus according to claim 1, wherein:
    the personal identification apparatus is attached to a part of an automobile, and
    if the personal identification is successful, control of the automobile becomes possible.

14. A personal identification apparatus comprising:
    a light source for irradiating light on a finger;
    an image pickup unit for picking up an image of light transmitted by a finger under influence of external light, the light transmitted by the finger being produced by either said external light alone or a combination of said external light and the light irradiated by said light source; and a processing unit for conducting personal identification by extracting blood vessels from the image picked up by said image pickup unit;

wherein said processing unit controls at least one of a light source power control unit for changing power of light sources and a sensitivity control unit for changing an amplification factor of image pickup elements in said image pickup unit, based on information of the image picked up by said image pickup unit.

15. A personal identification apparatus comprising:

a light source for irradiating light on a finger;

an image pickup unit for picking up an image of light transmitted by a finger under influence of external light, the light transmitted by the finger being produced by either said external light alone or a combination of said external light and the light irradiated by said light source;

a light source power control unit for changing power of said light source;

a sensitivity control unit for changing an amplification factor of image pickup elements in said image pickup; and a processing unit for controlling said light source power control unit and said sensitivity control unit;

wherein said processing unit extracts blood vessels from the image picked up by said image pickup unit and controls at least one of said light source power control unit and said sensitivity control unit, based on information of said image.

* * * * *